United States Patent [19]

Micetich et al.

[11] Patent Number: 4,507,239

[45] Date of Patent: Mar. 26, 1985

[54] PENICILLIN DERIVATIVES AND PROCESS FOR PREPARATION

[75] Inventors: Ronald J. Micetich, Sherwood Park, Canada; Shigeru Yamabe, Kobe, Japan; Shuichi Ueda, Tokushima, Japan; Naobumi Ishida, Hiroshima, Japan; Takeshi Ishizawa, Naruto, Japan

[73] Assignee: Taiho Pharmaceutical Company, Limited, Japan

[21] Appl. No.: 487,558

[22] Filed: Jun. 22, 1983

[30] Foreign Application Priority Data

Apr. 23, 1982 [JP] Japan .................................. 57-69142

[51] Int. Cl.³ .................. C07D 499/00; A61K 31/425
[52] U.S. Cl. ............................................. 260/245.2 R
[58] Field of Search .................. 260/245.2, 245.24; 424/270, 274

[56] References Cited

U.S. PATENT DOCUMENTS 4,218,374 8/1980 Kamiya et al. ............. 260/245.2 R
4,234,579 11/1980 Barth .................................... 424/246
4,256,733 3/1980 Barth .................................... 424/271

FOREIGN PATENT DOCUMENTS 2491071 4/1982 France .

*Primary Examiner*—Nicholas S. Rizzo
*Attorney, Agent, or Firm*—Murray, Whisenhunt and Ferguson

[57] ABSTRACT

A penicillin derivative represented by the following formula, a pharmaceutically acceptable salt thereof and an ester thereof:

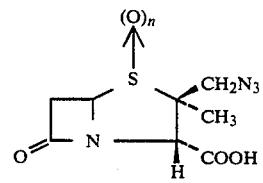

wherein n is 0, 1 or 2 and process for preparing the same.

8 Claims, No Drawings

PENICILLIN DERIVATIVES AND PROCESS FOR PREPARATION

This invention relates to penicillin derivatives and pharmaceutically acceptable salts thereof and esters thereof, and also to a process for preparing them.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve satisfactory effects against some types of microorganisms because of resistance of the microorganism to the β-lactam type antibiotics. The resistance thereof are usually attributable to β-lactamase produced by the microorganism. The β-lactamase is an enzyme which acts to cleave the β-lactam ring of the β-lactam type antibiotic, thereby causing the antibiotic to lose its antimicrobial activity. For this reason, the action of β-lactamase must be eliminated or inhibited so as to enable the β-lactam type antibiotic to produce satisfactory effects. The elimination or inhibition of the β-lactamase activity can be achieved by β-lactamase inhibitors, which are used conjointly with the β-lactam type antibiotic to increase the antimicrobial activity of the antibiotic.

It is an object of the present invention to provide novel compounds having β-lactamase inhibitory action.

It is another object of the invention to provide novel compounds useful as an intermediate for preparing the compounds having β-lactmase inhibitory action and represented by the formula

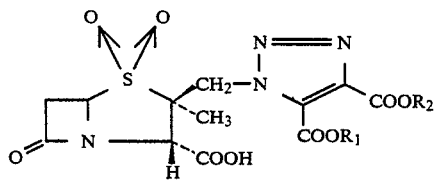

wherein $R_1$ and $R_2$ are lower alkyl group, respectively.

It is another object of the invention to provide processes for preparing the same.

It is a further object of the invention to provide a pharmaceutical composition having excellent β-lactamase inhibitory action.

It is an additional object of the invention to provide compositions which, when combined with β-lactam type antibiotics, can increase the antibacterial activity of the antibiotics.

The penicillin derivatives of the present invention are represented by the formula

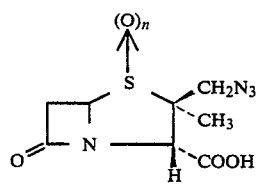

wherein n is 0, 1 or 2.

The pencillin derivatives of the present invention, pharmaceutically acceptable salts thereof and esters thereof are all novel compounds and have β-lactamase inhibitory properties, hence useful as β-lactamase inhibitory agents.

The penicillin derivatives of the invention, when used in combination with a known β-lactam type antibiotic, can increase the antimicrobial activity of the β-lactam type antibiotic.

Examples of antibiotics which can be used conjointly with the compounds of the present invention are β-lactam antibiotics which exhibit antibacterial action against gram-positive or gram-negative bacteria and which include commonly used penicillins such as ampicillin amoxicillin, hetacillin, ciclacillin, mecillinam, carbenicillin, sulbenicillin, ticarcillin, piperacillin, apalcillin, methicillin, mezlocillin and salts thereof; esters of penicillins such as bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftixozime, cefmenoxime, latamoxef, cefaclor, cefroxadine, cefatrizine, cefadroxil, cephaloglycin, and salts thereof. The β-lactam antibiotic are usually used in an amount of about 0.1 to about 10 parts by weight, preferably about 0.2 to about 5 parts by weight, per part by weight of the compound of the invention.

The derivatives of the present invention are also useful as an intermediate for preparing the compounds having β-lactamase inhibitory action and represented by the formula

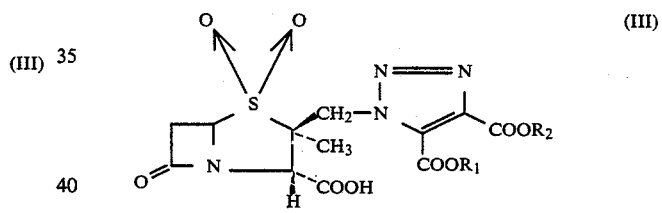

wherein $R_1$ and $R_2$ are lower alkyl group, respectively.

The compound of the formula (III) can be prepared according to the reaction equation given below.

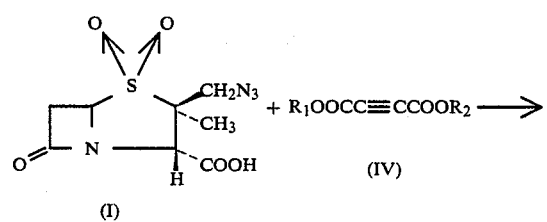

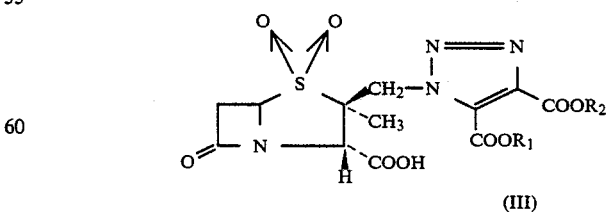

wherein $R_1$ and $R_2$ are as defined above. The process for preparing the compound of the formula (III) will be shown in detail in reference examples to be described later.

Examples of the pharmaceutically acceptable salts of the derivatives having the formula (I) are salts of sodium, potassium, lithium or like alkali metals; salts of calcium, magnesium or like alkaline earth metals; salts of cyclohexylamine, trimethylamine diethanolamine or like organic amines; salts of alginine, lysine or like basic amino acids; ammonium salts; etc. Examples of the esters of the present derivatives having the formula (I) include those which have carboxy protecting groups acceptable in the synthesis of the compounds of formula (III) and which are pharmaceutically acceptable. The term pharmaceutically acceptable ester refers to an ester which is easily hydrolyzed in vivo, the term ester to be hydrolyzed in vivo means a non-poisonous ester which rapidly decomposes in the blood or tissue of humans, producing the corresponding acid of the formula (I). Specific examples of the ester residues are methyl, ethyl, propyl, tert-butyl, pentyl, hexyl and like lower alkyl groups; methoxymethyl, ethoxymethyl, n-propyloxymethyl, iso-propyloxymethyl, n-butoxymethyl, iso-butoxymethyl and like lower alkoxymethyl groups; acetoxymethyl, propionyloxymethyl, n-butyryloxymethyl, iso-butyryloxymethyl, pivaloyloxymethyl, 1-acetoxyethyl, 1-pivaloyloxyethyl, 1-pivaloyloxypropyl, 1-propionyloxybutyl and like lower alkylcarbonyloxy-lower alkyl; cyclopentylcarbonyloxymethyl, cyclohexylcarbonyloxymethyl and like ($C_5$–$C_7$ cycloalkyl)carbonyloxy-lower alkyl groups; benzylcarbonyloxymethyl and like benzylcarbonyloxy-lower alkyl groups; benzoyloxymethyl, benzoyloxyethyl and like benzoyloxy-lower alkyl groups, etc. The term "lower" used in conjunction with "alkyl" or "alkoxy" is intended to indicate that each alkyl or alkoxy portion therein can contain 1 to 6 carbon atoms. The alkyl or alkoxy groupings can be straight- or branched-chain groups. Other examples of the penicillin carboxy protecting radicals include 3-phthalidyl, crotonolacton-4-yl, γ-butyrolacton-4-yl and like lactones; iodomethyl, 2,2-dibromoethyl, 2,2,2-trichloroethyl and like halogenated lower alkyl groups substituted with 1 to 3 halogen atoms such as Cl, Br, I; benzyl, p-methoxybenzyl, o-nitrobenzyl, p-nitrobenzyl, diphenylmethyl and like methyl groups which may be unsubstituted or may be substituted with methoxy or nitro on the phenyl; tetrahydropyranyl, dimethylaminoethyl, dimethylchlorosilyl, trichlorosilyl; (2-oxo-1,3-dioxoden-4-yl)methyl, (5-methyl-2-oxo-1,3-dioxoden-4-yl)methyl, (5-phenyl-2-oxo-1,3-dioxoden-4-yl)methyl and like (5-substituted or unsubstituted-2-oxo-1,3-dioxoden-4-yl)methyl groups, etc.

In the synthesis of penicillin compounds, a material is esterified to protect penicillin carboxyl groups present in the material. Usable in the present invention as the ester-protecting groups are those heretofore used, i.e., those which are sufficiently stable in the reaction and which does not permit the cleavage of the β-lactam ring in removal of the ester-protecting groups. Examples of such ester-protecting groups commonly used are methyl group substituted with 1 to 3 phenyl groups which may be unsubstituted or may be substituted with methoxy or nitro on the phenyl, and halogenated lower alkyl group.

Examples of such pharmaceutically acceptable ester which can be hydrolyzed in vivo are lower alkyl carbonyloxy-lower alkyl, cycloalkyl ($C_{5-7}$)-carbonyloxy-lower alkyl, benzylcarbonyl-lower alkyl-benzyloxy-lower alkyl, phthalidyl, lactones(5-substituted or unsubstituted-2-oxo-1,3-dioxoden-4-yl)methyl.

Examples of the present compound are: 2β-azidomethyl-2α-methylpenam-3α-carboxylic acid-1,1-dioxide, 2β-azidomethyl-2α-methylpenam-3α-carboxylic acid-1-oxide, and 2β-azidomethyl-2α-methylpenam-3α-carboxylic acid, and pharmaceutically acceptable salts thereof and esters thereof.

The penicillin derivatives of the present invention having the formula (I) can be prepared according to the reaction scheme shown below:

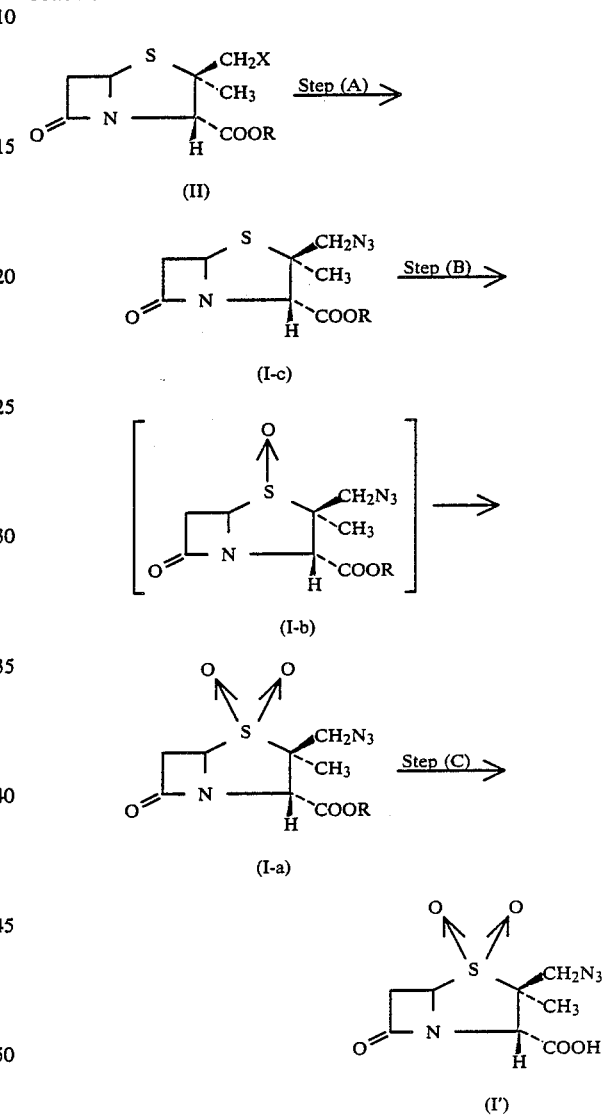

In the foregoing formulae, X represents chlorine atom or bromine atom and R represents penicillin carboxy protecting group.

The penicillin carboxy protecting groups expressed by R are acceptable in the synthesis of the compounds of formula (III).

The steps (A), (B) and (C) of the foregoing process will be described below in detail.

Step (A)

A penicillanic acid derivative of the formula (II) is reacted with a metal azide tor provide a compound of the formula (I-c). The reaction is conducted in a suitable solvent by reacting a known penicillanic acid derivative of the formula (II) with a metal azide in an amount of about 1 to about 50 moles, preferably about 1 to about 10 moles, per mole of the derivative of the formula (II). Examples of the metal azide which can be used include those commonly employed in the art such as sodium azide, potassium azide and like azides of alkali metals, and barium azide and like azides of alkaline earth metals. The solvents useful in the reaction are not particularly limited and include any of those which do not affect the reaction, such as dimethylformamide, ethyl acetate, acetone, dichloromethane, tetrahydrofuran, dioxane, methanol, ethanol and like organic solvents. These solvents are used singly or in mixture, and also can be employed as mixed with water. The reaction proceeds usually at a temperature between about −20° to about 100° C., preferably about 0° to about 60° C. After completion of the reaction, the resulting product can be used in subsequent procedure without isolation or alternatively after isolation and purification by a conventional method.

Step (B)

The compound of the formula (I-c) obtained in step (A) is oxidized to sulfoxide wof the formula (I-d) as an intermediate and eventually to dioxide of the formula (I-a). The oxidation is carried out by employing a commonly used oxidizing agent such as permanganic acid, periodic acid, peracetic acid, performic acid, trifluoro peracetic acid, perbenzoic acid, m-chloro perbenzoic acid, hydrogen peroxide or the like. The oxidizing agent can be used in large excess, and may be employed preferably in an amount of about 1 to about 2 moles per mole of the compound of the formula (I-c). The reaction is usually carried out in a suitable solvent. Useful solvents include any of those which do not affect the reaction such as chloroform, pyridine, tetrahydrofuran, dioxane, methylene chloride, carbon tetrachloride, acetic acid, formic acid, dimethylformamide, etc.

The reaction temperature is not particularly limited, but the reaction is usually conducted at about −20° to about 50° C., preferably about 0° to about 30° C.

Depending upon the kind of the penicillin carboxy protecting group, the compounds of the formula (I-c) or (I-a) obtained in step (A) or (B) may be a pharmaceutically acceptable ester of the penicillin derivatives of the present invention having the formula (I) which can be hydrolyzed in vivo. However, if the compounds of the formulae (I-a) and (I-c) are not the contemplated pharmaceutically acceptable ester derivatives of the formula (I), the compounds of the formulae (I-c) or (I-a) are subjected to de-esterification as in step (C) to form a dioxide derivative of the formula (I′) which, in turn, is converted in the conventional manner into a pharmaceutically acceptable salt or ester thereof which can be hydrolyzed in vivo. The esterification involved is carried out by a usual method. The compound of the formula (I-c) or (I-a) can be made into an ester which can be hydrolyzed in vivo or a pharmaceutically acceptable salt thereof by the conventional ester interchange or salt-forming reaction.

Step (C)

The compound of the formula (I-a) is subjected to de-esterification without or after isolation from the reaction mixture obtained in step (B), whereby dioxide of the formula (I′) is obtained.

Although not shown in the foregoing reaction scheme, following the general procedure of step (C) and using the compound of the formula (I-b) or (I-c) in place of the compound of the formula (I-a) as a starting material, there is provided the corresponding desired penicillin derivatives of the invention in the form of free acid, i.e. the derivatives of the following formulae:

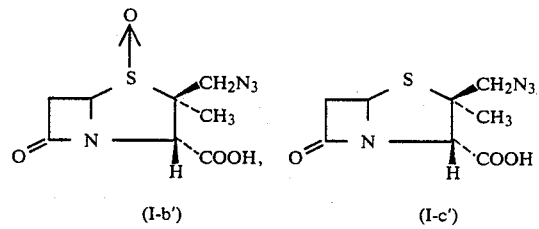

The de-esterification can also be carried out without or after isolating the starting materials of the formula (I-b) or (I-c) from the reaction mixture.

As the de-esterification method, reduction, hydrolysis, treatment with an acid and like method can be employed for converting the carboxy protecting group to carboxyl group. For example, if the carboxy protecting group is an active ester, the reaction frequently proceeds with ease under mild hydrolysis conditions or by merely bringing the ester into contact with water. The reduction method is employed when the carboxy protecting group is trichloroethylbenzyl, p-nitrobenzyl, diphenyl methyl or the like. Treatment with an acid is adopted when the carboxy protecting group is 4-methoxybenzyl, tert-butyl, trityl, diphenylmethyl, methoxymethyl, tetrahydropyranyl or the like.

The reduction can be conducted by treating the ester of the formula (I) with a mixture of (a) zinc, zinc-amalgam or like metal and/or chromium chloride, chromium acetate or like chromium salt and (b) formic acid, acetic acid or like acid. Alternatively, the reduction can be conducted with use of a catalyst in hydrogen atomosphere in a solvent. Examples of the catalysts are platinum, platinum oxide, palladium, palladium oxide, palladium-barium sulfate, palladium-calcium carbonate, palladium-carbon, nickel oxide, Raney-nickel, etc. The solvents are not particularly limited so far as they do no affect the reaction, and include methanol, ethanol and like alcohols; tetrahydrofuran, dioxane and like ethers; ethyl acetate and like esters; acetic acid and like fatty acids; and a mixture of these organic solvents and water.

The acids useful for eliminating the carboxy protecting group of the ester of the formula (I) are formic acid, acetic acid and like lower fatty acids; trichloroacetic acid, trifluoroacetic acid and like trihalogenated acetic acids; hydrochloric acid, hydrofluoric acid and like hydrohalogenic acids; p-toluenesulfonic acid, trifluoromethane-sulfonic acid and like organic sulfonic acids; and a mixture of these. In this reaction, when the acid used is in a liquid state and acts also as a solvent, it is not necessary to use other solvents. However, dimethylformamide, dichloromethane, chloroform, tetrahydrofuran, acetone and like solvents which do not affect the reaction may be used.

The penicillin derivative of the present invention having the formula (I), i.e., the derivative of the formula (I′) and the derivative in the form of free acid which corresponds to the starting compound of the formula (I-b) or (I-c), can be transformed by the salt-forming reaction or esterification commonly employed in the art into a pharmaceutically acceptable salt or ester which is hydrolyzed in vivo.

If the ester residue is, for example, 3-phthalidyl, crotonolacton-4-yl, γ-butyrolacton-4-yl or like group, the penicillin derivative of the formula (I) can be alkylated by using 3-halogenated phthalide, 4-halogenated crotonolactone, 4p-halogenated-γ-butyrolactone or the like. Suitable halogens of the foregoing halides include chlorifne, bromine, iodine, etc. The reaction is carried out by dissolving the salt of the penicillin derivative of the formula (I) in N,N-dimethylformamide or like suitable polar organic solvent and adding an approximately equimolecular amount of a halide to the solution. The reaction temperature ranges from about 0° to about 100° C., preferably from about 15 to about 35° C. Suitable salts of the penicillin derivative to be used in the esterification are salts of sodium, potassium or like alkali metals; salts of triethylamine, ethyldiisopropylamine, N-ethylpiperidine, N,N-dimethylaniline, N-methylmorpholine or like tertiary amines, etc. After completion of the reaction, the contemplated product can be easily separated by the conventional method and also can be purified, when required, by recrystallization, thin layer chromatography, column chromatography or like method.

The penicillanic acid derivative of the present invention, a pharmaceutically acceptable salt thereof and ester thereof which is hydrolyzed in vivo are mixed with a suitable antibiotic substance to form a preparation which is orally or parenterally administered. Alternatively, the present compound and a suitable antibiotic can be separately administered. Thus the derivatives of the formula (I) can be used for treating infections disease of human beings and other animals.

The composition of the present invention may be made into tablets, pills, capsules, granules, powders, syrups, lozenges, solutions, suspensions, etc. for oral administration and aqueous, suspending or water-soluble preparations for intravenous, subcutaneous or intramuscular injections.

Carriers useful in formulating the preparations are those commonly used pharmaceutically acceptable nontoxic carriers such as gelatin, lactose, starch, magnesium stearate, talc, vegetable oil, animal oil, polyalkylene glycol, etc. The carrier may be used with other additives such as diluents, binders, buffer agents, preservatives, glazes, disintegrators, coating agents, etc.

The daily dose of the preparation can be appropriately determined and is not particularly limited. Preferably the daily dose is such that the total amount of the present compound and β-lactam antibiotic is about 1 to about 200 mg/Kg body weight for oral administration and about 1 to about 100 mg/Kg body weight for parenteral administration.

The present invention will be described below in more detail with reference to examples given below.

EXAMPLE 1

Preparation of benzhydryl
2β-azidomethyl-2α-methylpenam-3α-carboxylate

An aqueous solution of 2.38 g of sodium azide and 25 ml of water was added to a solution of benzhydryl 2β-chloromethyl-2α-methylpenam-3α-carboxylate (2.44 g) in dimethylformamide (100 ml). The mixture was stirred at room temperature for 4 hours. The resulting reaction mixture was poured into water and the mixture was extracted with ether. The ether layer was washed with water and concentrated to provide 2.2 g of the contemplated product as oil in 89% yield.

Infrared absorption spectrum (nujol) νmax (cm$^{-1}$): 2120, 1812, 1765

Nuclear magnetic resonance spectrum (CDCl$_3$) δ(ppm): 1.30 (3H, s), 3.25 (2H, m), 3.42 (1H, d), 3.63 (1H, d), 4.75 (1H, s), 4.76 (1H, m), 7.00 (1H, s), 7.40 (10H, s)

EXAMPLE 2

Preparation of benzhydryl
2β-azidomethyl-2α-methylpenam-3α-carboxylate

An aqueous solution of 2.38 g of sodium azide and 25 ml of water was added to a solution of benzhydryl 2β-bromomethyl-2α-methylpenam-3α-carboxylate (2.71 g) in acetone (100 ml). The mixture was stirred at room temperature for 5 hours. The acetone was removed by distillation and the residue was extracted with ether. The extract was concentrated to provide 2.15 g of the contemplated product as oil in 86% yield.

The infrared absorption spectrum and nuclear magnetic resonance spectrum of the product obtained above were identical with those of the product prepared in Example 1.

EXAMPLE 3

Preparation of benzhydryl
2β-azidomethyl-2α-methylpenam-3α-carboxylate
1,1-dioxide To a solution of benzhydryl 2β-azidomethyl-2α-methylpenam-3α-carboxylate (2.22 g) in a mixture of acetic acid (75 ml) and water (12 ml) was added potassium permanganate (1.9 g). The mixture was stirred at room temperature for 4 hours. The excess potassium permanganate was destroyed by 30% hydrogen peroxide and the reaction mixture diluted with excess ice water. The precipitate was collected by filtration, and washed with water. The resulting product was dissolved in ether and the ether extract was washed with an aqueous solution of sodium bicarbonate and brine. Concentration gave 1.49 g of the contemplated product in 62.2% yield.

Infrared absorption spectrum (nujol) νmax (cm$^{-1}$): 2120, 1812, 1765

Nuclear magnetic resonance spectrum (CDCl) δ(ppm): 1.18 (3H, s), 3.50 (2H, d), 3.72 (1H, d), 3.93 (1H, d), 4.60 (1H, m), 4.65 (1H, s), 7.00 (1H, s), 7.36 (10H, s)

EXAMPLE 4

Preparation of sodium
2β-azidomethyl-2α-methylpenam-3α-carboxylate-1,1-dioxide

A 100 mg quantity of benzhydryl 2β-azidomethyl-2α-methylpenam-3α-carboxylate-1,1-dioxide was dissolved in a mixture of 50 ml of tetrahydrofuran and 50 ml of water and 50 mg of 10% palladium charcoal was added. The mixture was hydrogenated at room temperature under a pressure of 1 kg/cm$^2$. After absorption of the hydrogen was completed, the reaction mixture was filtered and the tetrahydrofuran was removed from the filtrate by distillation. To the residue was added 19.1 mg of sodium bicarbonate. The aqueous mixture was washed with chloroform and was chromatographed with a column of high porous polymer and eluted with water-10% acetone in water (gradient). The liquid thus obtained was freeze-dried to afford 21 mg of sodium 2β-azidomethyl-2α-methylpenam-3α-carboxylate as white powder in 37.3% yield.

Infrared absorption spectrum (KBr) νmax (cm$^{-1}$): 2140, 1785, 1630

Nuclear magnetic resonance spectrum (D$_2$O)

δ (ppm): 1.51 (3H, s), 3.36 (1H, dd), 3.64 (1H, dd), 4.00 (2H, s), 4.27 (1H, s), 4.95 (1H, dd)

EXAMPLE 5

Preparation of potassium 2β-azidomethyl-2α-methylpenam-3α-carboxylate-1,1-dioxide Benzhydryl 2β-azidomethyl-2α-methylpenam-3α-carboxylate-1,1-dioxide (110 mg) was dissolved in 2 ml of formic acid. The solution was left to stand for 10 minutes and freeze-dried. The residue was dissolved in a buffer solution of phoshoric acid (0.2M) with its pH adjusted to 7.2 using potassium phosphate mono- basic and potassium phosphate dibasic. The aqueous mixture was washed with chloroform and was chromatographed with a column of high porous polymer and eluted with water-10% acetone in water (gradient). The liquid thus obtained was freeze-dried to provide 25 mg of potassium salt of 2β-azido-2α-methylpenam-3α-carboxylate as white powder in 37.9% yield.

Infrared absorption spectrum (KBr) νmax (cm$^{-1}$): 2140, 1785, 1630

Nuclear magnetic resonance spectrum (D$_2$O)

δ(ppm): 1.52 (3H, s), 3.37 (1H, dd), 3.65 (1H, dd), 4.02 (2H, s), 4.29 (1H, s), 4.96 (1H, dd)

The compounds of the present invention obtained above were checked for pharmacological activity in the following manner.

(1) β-lactamase inhibitory activity

The compounds of the present invention obtained in the examples were tested by pH Stat method (Journal of Pharmaceutical Science, Vol. 61, No. 10, pp 1954 to 1958, published in 1972) for inhibitory activity against penicillinase (β-lactamase) from Bacillus SP.

The test results revealed that the sodium 2β-azidomethyl-2α-methylpenam-3α-carboxylate-1,1-dioxide had a 50%-β-lactamase inhibitory concentration (IC$_{30}$) of $4 \times 10^{-6}$M. The other derivatives obtained in the other examples were found to have similar values in IC$_{50}$.

(2) Antibacterial activity (synergistic effects attainable by the combined use of the present compounds and ampicillin or mecillinam)

The compounds of the present invention, ampicillin and mecillinam, each singly used, were checked for minimal inhibitory concentration (MIC) against the bacteria listed in Table 1 given below by the standard method of Japan Society of Chemlotherapy (Chemotherapy, Vol. 29, No. 1 p 76 to 79). The MICs of ampicillin or mecillinam as combined with the present compounds (10 g/ml) were also measured, against the same bacteria. Mueller Hinton Broth (Difco) was used as the growth medium and Mueller Hinton Agar (Difco) as the medium measuring the MIC. Table 1 below shows the results.

The bacteria used in the tests are those heretofore known and preserved in a depository, and are all offered by Dr. Nishino at Department of Microbiology, Kyoto College of Pharmacy except *P. Vulgaris*.

TABLE 1

| | | MIC (kg/ml) | | | | | |
|---|---|---|---|---|---|---|---|
| | | Test of Ampicillin and/or Compound of Example 4 | | | Test of Mecillinam and/or Compound of Example 4 | | |
| Test Bacteria | Amount of Innoculum size(cell/me) | Ampicillin | Compound of Ex. 4 | Combined Use of Ampicillin and Comp. of Ex. 4 (10 μg/ml) | Mecillinam | Compound of Ex. 4 | Combined Use of Mecillinam and Com. of Ex. 4 (10 μg/ml) |
| S. aureus S-54 | 10$^8$ | 100 | >100 | 0.2 | 800 | >100 | 50 |
| S. aureus No. 80 | 10$^8$ | 100 | >100 | 0.2 | 800 | >100 | 25 |
| E. coli No. 21 | 10$^8$ | — | — | — | >800 | >100 | 12.5 |
| P. mirabilis 121-1 | 10$^6$ | 200 | 50 | 6.25 | — | — | — |
| P. vulgaris IID OX-19 | 10$^8$ | — | — | — | 400 | 25 | 3.13 |

EXAMPLE 6

Preparation of p-nitrobenzyl 2β-azidomethyl-2α-methylpenam-3α-carboxylate

The procedure of Example 1 was repeated with the exception of using as the starting material p-nitrobenzyl 2β-chloromethyl-2α-methylpenam-3α-carboxylate, affording the above contemplated compound.

Infrared absorption spectrum (KBr) νmax (cm$^{-1}$): 2120, 1798, 1760

Nuclear magnetic resonance spectrum (CDCl$_3$)

δ(ppm): 1.40 (3H, s), 3.12 (1H, dd), 3.50 (2H, s), 3.62 (1H, dd), 4.83 (1H, s), 5.29 (2H, s), 5.36 (1H, dd), 7.56 (2H, d), 8.26 (2H, d),

EXAMPLE 7

Preparation of p-nitrobenzyl 2β-azidomethyl-2α-methylpenam-3α-carboxylate-1,1-dioxide The procedure of Example 3 was followed with the exception of using as the starting material p-nitrobenzyl 2β-azidomethyl-2α-methylpenam-3α-carboxylate, giving the above contemplated compound.

Infrared absorption spectrum (KBr) νmax (cm$^{-1}$): 2120, 1770

Nuclear magnetic resonance spectrum (CDCl$_3$)

δ(ppm): 1.42 (3H, s), 3.45–3.60 (2H, m), 3.75 (1H, d), 3.96 (1H, d), 4.56–4.75 (1H, m), 4.64 (1H, s), 5.33 (2H, s), 7.56 (2H, d), 8.26 (2H, d)

REFERENCE EXAMPLE 1

Preparation of benzhydryl 2β-(4,5-dimethoxy-carbonyl-1,2,3-triazol-1-yl)methyl-2α-methylpenam-3α-carboxylate-1,1-dioxide A mixture of 0.870 g of benzhydryl 2β-azidomethyl-2α-methylpenam 3α-carboxylate-1,1-dioxide and 0.618 g of dimethylacetylene-dicarboxylate was stirred in 15 ml of benzene with reflux in nitrogen atmosphere for 18 hours. The solvent was removed by distillation. The residue was chromatographed on silica gel column with ethyl acetate-chloroform (1:3) as eluate, giving 0.495 g of the contemplated product as light yellow crystals in 44% yield which melts at 75° to 77° C.

Infrared absorption spectrum (KBr) νmax (cm$^{-1}$): 1800, 1735

Nuclear magnetic resonance spectrum (CDCl$_3$) δ(ppm): 1.20 (3H, s), 3.48 (2H, t), 3.97 (3H, s), 3.98 (3H, s), 4.59 (1H, m), 4.95 (1H, s), 5.26 (2H, s), 6.97 (1H, s), 7.36 (10H, s)

REFERENCE EXAMPLE 2

Preparation of sodium 2β-(4,5-dimethoxycarbonyl-1,2,3-triazol-1-yl)methyl-2α-methylpenam-3α-carboxylate-1,1-dioxide Hydrogenation was conducted at ordinary pressure and room temperature by using 100 ml of tetrahydrofuran, 100 ml of water, 116 mg of benzhydryl 2β-(4,5-dimethoxycarbonyl-1,2,3-triazol-1-yl)-methyl-2α-methylpenam-3α-carboxylate-1,1-dioxide, 58 mg of 10% palladium charcoal and 17 mg of sodium bicarbonate. After the absorption of the hydrogen was completed, the reaction mixture was filtered and the tetrahydrofuran was removed from the filtrate at reduced pressure by distillation. The residue was washed with chloroform and the aqueous solution was concentrated at reduced pressure. The aqueous mixture was washed with chloroform and was chromatographed with a column of high porous polymer and eluted with water-10% acetone in water (gradient). The liquid thus obtained was freeze-dried to obtain 53 mg of the contemplated product as white powder in 60% yield. The white powder decomposed at over 165° C.

Infrared absorption spectrum (KBr) νmax (cm$^{-1}$): 1785, 1735, 1630

Nuclear magnetic resonance spectrum (D$_2$O) δ(ppm): 1.41 (3H, s), 3.40 (1H, dd), 3.80 (1H, dd), 3.98 (3H, s), 4.05 (3H, s), 4.51 (1H, s) 5.03 (1H, dd), 5.48 (2H, d)

Given below are examples of preparation of the present antibacterial compositions.

| Preparation Example 1 | |
|---|---|
| Ampicillin | 200 mg |
| Compound of Example 4 | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into capsule.

| Preparation Example 2 | |
|---|---|
| Amoxycillin | 100 mg |
| Compound of Example 5 | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

| Preparation Example 3 | |
|---|---|
| Pivmecillinam | 70 mg |
| Compound of Example 4 | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |
| Total | 220 mg |
| | (amount per tablet) |

The above ingredients are formulated in the proportions listed above into a tablet.

| Preparation Example 4 | |
|---|---|
| Compound of Example 5 | 120 mg |
| Hydroxypropyl cellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

We claim:

1. A penicillin derivative represented by the following formula:

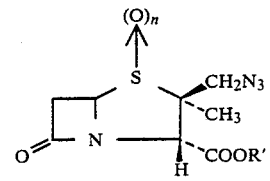

wherein n is 0, 1 or 2, and R' is hydrogen; or a pharmaceutically acceptable salt thereof.

2. A penicillin derivative as claimed in claim 1, wherein said pharmaceutically acceptable salt is an alkali metal salt, an alkaline earth metal salt, an ammonium salt, a cyclohexylamine salt, a trimethylamine salt, a diethanol amine salt, an arginine salt or a lysine salt.

3. A pencillin derivative represented by the following formula:

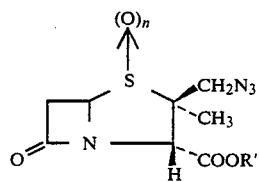

wherein n is 0, 1 or 2 and R' is a carboxy protecting group.

4. The penicillin derivative as claimed in claim 3, wherein R' is $C_1$–$C_6$ alkyl, $C_1$–$C_6$ alkoxy methyl, $C_1$–$C_6$ alkyl-carbonyloxy-$C_1$–$C_6$ alkyl, ($C_5$–$C_7$ cycloalkyl)-carbonyloxy-$C_1$–$C_6$ alkyl, benzylcarbonyloxy-$C_1$–$C_6$ alkyl, benzoyloxy-$C_1$–$C_6$ alkyl, 3-phthalidyl, crotonolacton-4-yl, γ-butyrolacton-4-yl, $C_1$–$C_6$ alkyl substituted with 1 to 3 halogen atoms, phenyl-methyl group which may be unsubstituted or may be substituted with methoxy or nitro on the phenyl, diphenyl methyl, tetrahydropyranyl, dimethylaminoethyl, dimethylchlorosilyl, trichlorosilyl, or (unsubstituted or 5-methyl substituted or 5-phenyl substituted-2-oxo-1, 3-dioxoden-4-yl)-methyl.

5. A process for preparing a penicillin derivative of the formula:

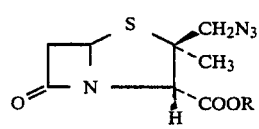

wherein
R is a carboxy protecting group, the process comprising: contacting a compound of the formula

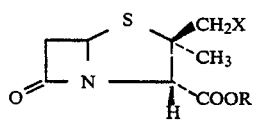

wherein X is chlorine or bromine and R is as defined above, with an alkali metal azide or an alkaline earth metal azide to produce the compound of the formula

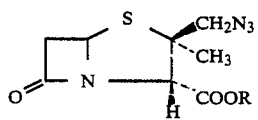

wherein R is as defined above.

6. A process for preparing a penicillin derivative of the formula

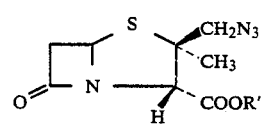

wherein R' is hydrogen, the process comprising contacting a comound of the formula

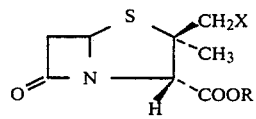

wherein X is chlorine or bromine and R is a carboxy protecting group, with an alkali metal azide or an alkaline earth metal azide to produce a compound of the formula

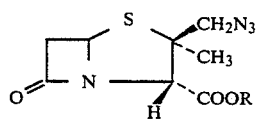

wherein R is as defined above; and contacting the compound of the formula (I-c) with a de-esterifying agent.

7. A process for preparing a penicillin derivative of the formula

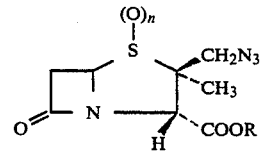

wherein n = 1 or 2, and R is a carboxy protecting group, the process comprising:
contacting a compound of the formula

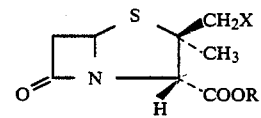

wherein X is chlorine or bromine and R is defined above, with an alkali metal azide or an alkaline earth metal azide to produce a compound of the formula

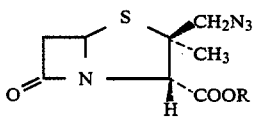

wherein R is as defined above; and
contacting the compound of the formula (I-c) with an oxidizing agent to produce a compound of the formula

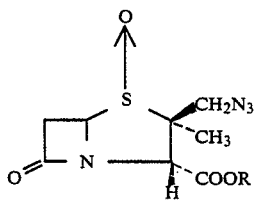

or

-continued

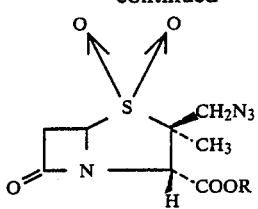
(I-a)

wherein R is as defined above.

8. A process for preparing a penicillin derivative of the formula

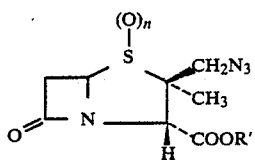

wherein n is 1 or 2 and R' is hydrogen, the process comprising:

contacting a compound of the formula

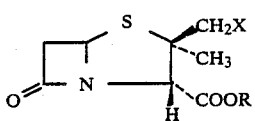

wherein X is chlorine or bromine and R is a carboxy protecting group, with an alkali metal azide or an alkaline earth metal azide to produce a compound of the formula

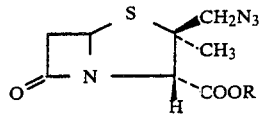
(I-c)

wherein R is as defined above;
contacting the compound of the formula (I-c) with an oxidizing agent to produce a compound of the formula (I-b)

or (I-a)

wherein R is as defined above; and
contacting the compound of the formula (I-b) or (I-a) with a de-esterifying agent.

* * * * *

UNITED STATES PATENT AND TRADEMARK OFFICE
CERTIFICATE OF CORRECTION

PATENT NO. : 4,507,239

DATED : April 22, 1983

INVENTOR(S) : Ronald G. Micetich, et al.

It is certified that error appears in the above-identified patent and that said Letters Patent is hereby corrected as shown below:

In the heading of the patent, after "[22] Filed:", delete "June 22, 1983" and insert therefor -- April 22, 1983 -- .

Signed and Sealed this

Twenty-seventh Day of August 1985

[SEAL]

Attest:

DONALD J. QUIGG

Attesting Officer     Acting Commissioner of Patents and Trademarks